United States Patent [19]

Gibson

[11] 4,268,697

[45] May 19, 1981

[54] SYNTHESIS OF LONG-CHAIN ALKANES HAVING TERMINAL FUNCTIONALITY

[75] Inventor: Thomas W. Gibson, Cincinnati, Ohio

[73] Assignee: The Procter & Gamble Company, Cincinnati, Ohio

[21] Appl. No.: 50,839

[22] Filed: Jun. 21, 1979

[51] Int. Cl.[3] .................... C07C 29/72; C07C 19/07; C07C 19/02

[52] U.S. Cl. .................................. 568/911; 570/241; 570/252; 570/257

[58] Field of Search ............... 585/646; 260/429.3, 260/652 R; 568/911

[56] References Cited

U.S. PATENT DOCUMENTS

| | | | |
|---|---|---|---|
| 4,078,012 | 3/1978 | Plewett et al. | 585/646 |
| 4,125,567 | 11/1978 | Kidwell et al. | 260/429.3 |
| 4,151,186 | 4/1979 | Kidwell et al. | 260/429.3 |

OTHER PUBLICATIONS

Calderon et al., "Angew Chem. Int. Ed. Engl." vol. 15, (1976), pp. 401–409.
Bailey "Catalysis Reviews" 3:37 (1970).
Mol et al. "Advances In Catalysis" 24, 131 (1975).
Calderon, "Acts. of Chem. Res.", 5, 127 (1972).
Bertello et al., "JACS" 97, 228 (1975).
Hart et al., "JACS" 97:679 (1975).
Brown et al., "JACS" 81:6434 (1959).
Logan, "J. Org. Chem." 26:3657 (1961).
Lahenger et al., "JACS" 97:3851 (1975).
Hart et al., "J.A.C.S.", vol. 96 (1974), pp. 8115–8116.
Blackburn et al., "Tetrahedron Letters", 1975, pp. 3041–3044.
Schwartz et al., "Angew. Chem. Int. Ed. Engl." vol. 15 (1976) No. 6, pp. 333–340.

Primary Examiner—Joseph E. Evans
Attorney, Agent, or Firm—Michael J. Roth; Jerry J. Yetter; Richard C. Witte

[57] ABSTRACT

A process for preparing primary substituted n-alkane compounds, comprising contacting the olefin product of an olefin metathesis reaction having an alpha-olefin as the reactant with a bis-cyclopentadienyl zirconium hydrohalide and, after contacting the product of the olefin-zirconium hydrohalide reaction with an electrophilic reagent, recovering said primary substituted n-alkane compound.

1 Claim, No Drawings

SYNTHESIS OF LONG-CHAIN ALKANES HAVING TERMINAL FUNCTIONALITY

TECHNICAL FIELD

The commercial testing and use of long-chain organic compounds has been restricted by the limited availability of compounds having a carbon chain length of greater than about $C_{20}$–$C_{22}$. Where examination of compounds of greater carbon chain length is desired, resort must usually be made to synthetic chemistry to extend the chain lengths of shorter chain compounds since the long-chain compounds are only present in small amounts in natural products such as waxes and oils.

The synthetic techniques for producing long-chain compounds are generally laborious and inconvenient. Often, reactions in which short-chain carbon compounds would be used to extend chain lengths are ineffective where longer chain compounds are the starting materials. Carbon chains can be extended two carbons at a time using malonic acid synthesis procedures. Grignard reagents and ethylene or propylene oxide can be used to extend chains two to three carbons at a time, but side reactions producing secondary substitution often occur. Chains can be extended by eight carbons through the multi-step reaction of acid chloride and thiophene in two successive Wolf-Kischner reactions followed by Raney-Nickel reduction. Where long-chain starting materials are used, reactions of organolithium, -sodium and -potassium compounds with aldehydes and carboxylic acids are unsuccessful. Similarly, the reaction of alkyl halides with organolithium compounds has been unsuccessful where long-chain compounds are involved (see generally, Welebir, Ph.D. Diss., American Univ. 1978, Univ. Microfilms 7,814,929). Additionally, unless a particular reaction produces a pure long-chain compound of uniform carbon chain length, recovery of the desired compound is very difficult since the physical and chemical properties of long-chain homologs are so similar.

The present invention embodies the discovery that an olefin metathesis (or olefin disproportionation) reaction can be coupled with a hydrometallation reaction to produce long-chain terminal substituted n-alkanes of high purity and with good yields. By the practice of the instant invention, chain length is extended dramatically in one reaction while terminal substitution is easily obtained through a second. Additionally, the present invention embodies the discovery that the hydrometallation reagent can be generated in situ; it need not be recovered and purified before use. The metallation reagent thus generated produces pure alkanes with terminal substitution more rapidly, with greater purity and convenience, and at lower temperatures than where organoboron and organoaluminum compounds are used. Through the practice of the process, long-chain carbon compounds such as 1- triacontanol, recently discovered to be an effective plant growth stimulant (Science, Mar. 25, 1977, pp. 1339–1341), are now readily available for testing and commercial use.

BACKGROUND ART

The olefin metathesis reaction, also known as the olefin disproportionation reaction, has been used for some time in the petroleum industry to metathesize propane into polymerization grade ethene and high quality butenes. Metatheses of 1-octene to ethene and 7-tetradecene have been performed. Bailey, *Catalysis Reviews* 3:37 (1970). The catalysts necessary for the reaction are generally known, see, e.g. Bailey, above; Mol. et al., *Advances in Catalysis*, 24, 131 (1975); Calderon, *Acts. of Chem. Res.*, 5, 127 (1972); Calderon, et al., *Angew. Chem. Int. Ed.*, 15 401 (1976). Mol, et al. also describe the use of the metathesis reaction to form macrocyclic compounds and the production of detergent range linear alkenes from lower alkenes. These workers have typically confined their synthetic efforts to the production of alkenes.

The literature has recently described hydrometallation reactions, specifically hydrozirconation reactions, using bis-cyclopentadienyl zirconium hydrochloride (often abbreviated $Cp_2ZrHCl$). This compound adds across internal double bonds of an olefin and then migrates completely and rapidly to the end of the carbon chain. The terminal zirconium moiety can then be replaced by electrophilic groups under mild conditions. Hart, et al., *JACS* 96:8115 (1974); Bertelo, et al., *JACS* 97:228 (1975); Hart, et al., *JACS* 97:679 ;1 (1975); Lahenger, et al., *JACS* 97:3851 (1975); Blackburn, et al., *Tet. Ltr* 3041 (1975). The hydrozirconation reaction is a convenient replacement for more traditional reactions, such as hydroboration, for converting olefins into terminal functional alkanes. See, e.g., Brown, et al., *JACS* 81:6434 (1959) and Logan, *J. Org. Chem.* 26:3657 (1961).

None of the workers in the art appear to have appreciated the convenience and ease of preparation of terminal functional alkanes using the present process, especially as it relates to the long-chain alkanes.

DISCLOSURE OF THE INVENTION

The present invention encompasses a process for preparing primary substituted n-alkane compounds, comprising contacting an α-olefin with an olefin metathesis catalyst, contacting the product of that reaction with a bis-cyclopentadienyl zirconium, titanium or hafnium hydrohalide, and contacting the product of the zirconium, titanium or hafnium reaction with an electrophilic reagent to produce the primary substituted n-alkane compound which is then recovered. The outstanding feature of the present invention is that with certain reagents the second step of the process, the hydrometallation reaction, can take place in the solution in which the cyclopentadienyl metal hydrohalide is originally generated.

The process steps can be illustrated by the following reaction scheme for the synthesis of 1-iodotriacontane by hydrozirconation:

(a) Metathesis of 1-hexadecene to form 15-triacontene:

$$2H_3C(CH_2)_{13}CH=CH_2 \xrightarrow{WCl_6/Me_4Sn/EtAc} CH_2=CH_2 +$$
$$H_3C(CH_2)_{13}CH=CH(CH_2)_{13}CH_3$$

(b) Hydrozirconation of 15-triacontene to achieve terminal activity:

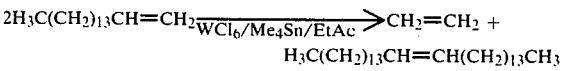

(i)

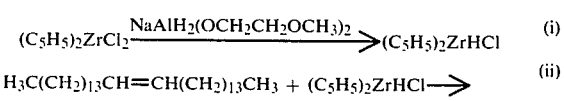

(ii)

(c) Iodination of hydrozirconated 15-triacontene to form 1-iodotriacontane

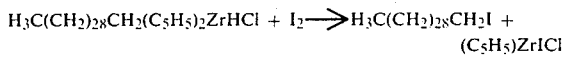

BEST MODE

The best mode of practicing the present invention is illustrated by the following synthesis of 1-iodotriacontane. The same procedure works equally well for the synthesis of other primary substituted n-alkane compounds.

a. Metathesis of 1-hexadecene: 1-hexadecene was dried by distillation from $CaH_2$ and stored under Argon. To 579 g. (2.50 moles) of the olefin in a 3-neck flask at 80° C. under an Argon atmosphere was added 4.8 g. (0.012 moles) of $WCl_6$, 5.1 g. (0.04 mole) of ethyl acetate, and 5.3 g. (0.03 mole) of $Me_4Sn$. Vigorous evolution of ethane began after a few minutes, gradually subsiding until after 2 hours a fresh batch of catalyst materials was added (0.008, 0.033, and 0.02 moles, respectively). After maintaining the reaction at 80° C. overnight, the mixture was cooled, neutralized with excess concentrated ammonium hydroxide and dissolved in hexane. The hexane solution was extracted thoroughly with water, dried over $Na_2SO_4$, and concentrated to a solid mass. Recrystallization from acetone gave 279 g. of 15-triacontene (m.p. 55° C.), approximately 98.8% pure by g.c. analysis.

b. Hydrozirconation/iodination of 15-triacontene: To 386.0 g. (1.32 moles) of $Cp_2ZrCl_2$ in 3 liters of THF (dried over $CaH_2$) under Argon was added 0.69 moles of $NaAlH_2$ $(OCH_2CH_2OCH_3)_2$ via syringe. After 2 hours, 277.1 g. (0.66 mole) of 15-triacontene was added, and the mixture heated to 40° C. for 48 hours.

c. Reaction with electophile: After cooling in an ice bath, 33.4 g. (1.32 moles) of iodine was added slowly so as to keep the temperature of the mixture below 30° C. After 4 hours at room temperature, the solvent was removed by distillation, the residue taken up in a large volume of hexane, filtered, and poured through 500 g. of silica gel. The eluate was crystallized from hexane to give 225.7 g. (63%) of 1-iodotriacontane, uncontaminated with olefin or internal iodide isomers. Crystallization of the residue from acetone gave an additional 63.7 g. of a 38:62 olefin:iodide mixture.

1-bromotriacontane can be prepared by substitution of N-bromosuccinimide for the iodine in Step b. The bromo- or iodotriacontane can be used to prepare long-chain surfactants such as ammoniohexanoates through reaction with ethyl-6-dimethylamino hexanoate. Unreacted olefin need not be removed from the reaction mixture since the precipitation of the quaternary ester from the reaction medium gives material free of olefin.

The plant growth stimulant 1 triacontanol can be conveniently prepared from the alkyl halide by reaction of 1-iodotriacontane with sodium acetate using phase transfer catalysis conditions followed by hydrolysis, or by reaction of the alkyl zirconium intermediate with peroxide or oxygen.

Similar results are obtained when bis-cyclopentadienyl titanium or hafnium halides are used in the foregoing process.

INDUSTRIAL APPLICABILITY

The first step of the reaction sequence uses an α-olefin of the formula $RCH=CH_2$. R is preferably n-alkyl to avoid the production of isomeric end products after the hydrometallation reaction and is most preferably greater than about $C_{11}$ n-alkyl. The reaction sequence can be performed using shorter chain olefins to prepare compounds of $C_{20}$ or less, but these compounds are already readily available from commercial sources.

The α-olefin is subjected to the conditions of an olefin metathesis reaction to produce ethene and an internal olefin of the formula $RCH=CHR$. This first reaction step extends the length of the carbon chain by nearly twice. Where the starting α-olefin is, for example, 1-hexadecene, the internal olefin product will have a carbon chain length of $C_{30}$.

The olefin metathesis reaction requires a catalyst. Bailey, *Catalysis Reviews* 3:37 (1970), incorporated herein by reference, provides a general discussion of olefin metathesis catalysts for olefin metatheses which can be used in the first step of the present process.

Many catalyst systems used in olefin metathesis reactions are heterogeneous such metathesis reaction-promoting catalysts are usually deposited on a high surface area refractory support. While useful in the present process for large scale commercial production, the heterogeneous catalysts have a disadvantage in that they usually must be synthesized since they are not commercially available, and they must also be activated, e.g. by heating at 550°–600° C. for several hours. Additionally, they are often poisoned by chemically active and polar compounds such as water, acetone, carbon monoxide and methanol.

Homogeneous catalyst systems are also known for olefin metathesis reactions and are preferred for use herein. Homogeneous catalysts reported in the literature include systems such as tungsten hexachloride/ethanol/ethylaluminum dichloride and tungsten hexachloride/n-butyl lithium. The literature reports obtaining homogeneous catalyst systems by the treatment of nitrosyl complexes of the formula $L_2Cl_2(NO)_2M$ (where M is molybdenum or tungsten and L is $((C_6H_5)_3P$, $C_5H_5N$, or $(C_6H_5)_3PO)$) with alkylaluminum halides.

Exemplary catalysts reported in the literature as having been used in olefin metathesis systems with α-olefins as the reactants include $[(C_6H_5)_3P]_2Cl_2Mo(NO)_2$ with $Me_3Al_2Cl_3$ (*JACS* 92, 528 (1970)); $R'_4N[Mo(CO)_5Cl]$ with $MeAlCl_2$ (*J. Catalysis* 30, 118 (1973)); $Re(CO)_5Cl$ with $EtAlCl_2$ (*Inorg. Chem.* 15, 2129 (1976)); $WCl_6$ with $SnMe_4$ (*Tet. Ltr.* 441 (1977)) and $Re_2O_7$ with $Al_2O_3$ (*J. Chem. Soc. Chem. Enr.* 198 (1977)).

The preferred metathesis catalyst system for use herein is homogeneous and is a mixture comprising a tungsten hexahalide, a tetraalkyl tin compound, and ethyl acetate. The tungsten hexahalide is preferably tungsten hexachloride or tungsten hexabromide and is most preferably tungsten hexachloride. The alkyl component of the tetraalkyl tin compound can be of mixed or uniform alkyl chain length; it is preferably lower alkyl, $C_1$–$C_4$, and most preferably methyl. The ethyl acetate serves as a mild base, and prevents the acid-catalyzed isomerization of the α-olefin by the tungsten hexahalide. The preferred catalyst system is very convenient to use since it comprises readily available compounds which require neither synthesis nor activation.

The first reaction step can take place in any inert organic solvent, e.g. tetrahydrofuran, benzene, or toluene. The time of reaction can vary and depends on the temperature at which the reaction is performed and the nature of the catalyst and alpha-olefin. Typical reaction temperatures can range from 0° C. or less to 100° C. or more and typical reaction times can vary from minutes to days.

The product of the first step in the reaction sequence is an internal olefin of the formula RCH=CHR. In the second step of the reaction sequence, this internal olefin is contacted with a bis-cyclopentadienyl zirconium, hafnium or titanium hydrohalide under hydrometallation conditions. During this second step, the metal compound apparently adds across the double bond and then migrates quickly and completely to the end of the carbon chain. In contrast to reactions in which organoboron and organoaluminum compounds are used to produce compounds having terminal functionality, hydrometallation reactions involving cyclo-pentadienyl titanium, zirconium and hafnium hydro-halides produce internal isomers less readily. This lack of isomerization is critical where long-chain alkanes are being synthesized since long-chain isomeric mixtures are difficult to resolve. The preferred metal is zirconium.

The preferred bis-cyclopentadienyl zirconium dihalide precursor of the hydrohalide is typically formed using standard organic procedures by the reaction of the appropriate zirconium tetrahalide, e.g. $ZrCl_4$, with a solution containing cyclopentadienyl anions (formed, for example, by the metallation of cyclopentadiene by reagents such as $C_6H_5Na$, butyl Li, and Li diethylamide in ether). The zirconium hydrohalide is then formed from the dihalide by reaction of the zirconium compound with a hydride donor, especially an organoaluminum compound. The organoaluminum compound can be an alkoxide of the formula $LiAlH(OR^1)_3$ wherein $R^1$ is alkyl and preferably lower alkyl ($C_1$-$C_5$), lithium aluminum hydride, or an oxyalkylene compound such as $NaAlH_2(OCH_2CH_2OCH_3)_2$. When the zirconium hydrohalide is generated in situ and is not isolated, lithium aluminum hydride is less desirable as the hydride donor than other organoaluminum compounds. Among the products of the reaction of $LiAlH_4$ with the zirconium dihalide is aluminum chloride which appears to interfere with the completeness of the hydrozirconation reaction. Apparently, the aluminum exchanges with the zirconium on the substituted olefin to yield an aluminum-substituted long-chain compound which ultimately produces undesirable internal isomer contaminants as a result of the slow migration of aluminum to the chain end.

Organoaluminum compounds of the formula $LiAlH(OR^1)_3$ can be prepared separately or in situ in the reaction vessel by reaction of the corresponding alkanol with lithium aluminum hydride. The compound wherein $R^1$ is t-butyl is commercially available, prepared from t-butyl alcohol and $LiAlH_4$, although very sensitive to hydrolysis on storage; the compound wherein $R^1$ is methyl is unstable but can be made for use from methanol and $LiAlH_4$.

The preferred aluminum hydride compounds are oxyalkylene compounds, especially $NaAlH_2(OCH_2CH_2OCH_3)_2$ which is relatively stable, is commercially available in 70% toluene solution and is known as "Vitride."

The bis-cyclopentadienyl zirconium hydrohalide can be prepared in advance and stored for later use. However, because bis-cyclopentadienyl zirconium hydrohalides react readily with moisture and air, some activity is lost in storage. The preferable and more convenient procedure is to prepare and use the zirconium hydrohalide in situ without isolating it from the reaction mixture.

The bis-cyclopentadienyl titanium and hafnium hydrohalides can be prepared from the corresponding tetrahalides, e.g. $TiCl_4$ or $HfCl_4$, using the same procedures as used to prepare the corresponding zirconium reagent.

Generally the reaction of the internal olefin produced by the first step in the reaction sequence and the metal hydrohalide can take place in any inert solvent, tetrahydrofuran, benzene, or toluene, for example. The reaction is typically performed at 20°-60° C. with a reaction time on the order of hours to days.

The third and final step in the reaction sequence is the preparation of the compound having a terminal functional group from the terminal cyclopentadienyl metal alkane. Terminal functionality is conveniently introduced by adding the desired electrophile to the reaction mixture resulting from the second step in the reaction sequence. Electrophilic reagents are known in chemistry as reagents capable of forming new bonds by accepting a pair of electrons, for example by addition to the reactant or by transfer of a proton. Examplary electrophiles useful herein include halogen compounds such as $m$-$ClC_6H_4CO_3H$, $C_6H_5ICl_2$, haloacids (e.g. HCl, HBr, HI), hypohalous acids (e.g. HOCl), $CH_3COCl$, $Cl_2$, $Br_2$, $I_2$, n-bromosuccinimide, carbon monoxide, HCN, nitriles, $NO_2$, peroxide compounds, ozone and oxygen. Reaction of the terminal metal alkane with a peroxide compound such as hydrogen peroxide, t-butyl hydroperoxide or oxygen, for example, will produce an n-alkanol while reaction with preferred halogen compounds such as iodine, bromine or n-bromosuccinimide will produce an n-bromoalkane or an n-iodoalkane. The terminal-substituted n-alkane can then be recovered using standard techniques or can be subjected to further reactions as desired.

The electrophilic reaction of the third step can be performed above or below room temperature and typical reaction times are on the order of minutes to hours. The invention is further illustrated by the following examples.

EXAMPLE I

Preparation of Tetratriacontanyl Iodide

Metathesis of 1-octadecene: 1-octadecene was dried by distillation from $CaH_2$ and stored under Argon. To 177.2 g. (0.70 moles) of the olefin in a 3-neck flask at 80° C. under an Argon atmosphere were added 2.92 g. (0.007 moles) of $WCl_6$, 2.46 g. (0.028 moles) of ethyl acetate, and 2.74 g. (0.015 moles) of $Me_4Sn$. Vigorous evolution of ethylene began after a few minutes, gradually subsiding until after 2 hours a fresh batch of catalyst materials was added (0.005, 0.022, and 0.01 moles, respectively). After maintaining the reaction at 80° C. overnight, the mixture was cooled, neutralized with excess concentrated ammonium hydroxide, and dissolved in hexane. The hexane solution was extracted thoroughly with water, dried over $Na_2SO_4$, and concentrated to a solid mass. Gas chromatographic analysis showed only 1-octadecene and 17-tetratriacontene in a 26:74 ratio. Recrystallization from acetone gave 81.6 g. (49% yield) of mainly trans-17-tetratriacontene, m.p. 63°-4°, approximately 96% pure by g.c. analysis.

To a solution of 44.8 g. (0.15 mole) of $Cp_2ZrCl_2$ in 800 ml. tetrahydrofuran under Argon was added 24.7 g. (0.086 mole) of $NaAlH_2(OCH_2Ch_2OCH_3)_2$ in benzene via syringe. After stirring 2 hours at room temperature, 36.8 g. (0.077 mole) of the olefin, 17-tetratriacontene, was added and the mixture kept at 40° C. for 7 days. After cooling in an ice bath, solid iodine (34.0g., 0.134 mole) was added. The mixture was filtered and the solvent removed in vacuum. NMR analysis indicated an olefin:iodide ratio of 25:75. The residue was dissolved in hexane and percolated through dry silica gel to remove impurities. Recrystallization from hexane gave 13.0 g. pure iodide, m.p. 75°–6° C. and 14.4 g. of a 58:42 olefin-:iodide mixture.

EXAMPLE II

Preparation of Tetracosyl Iodide

Metathesis of 1-tridecene: A mixture of 546 g. (3.0 moles) of 1-tridecene (distilled from $CaH_2$), 4.9 g. (0.015 mole) $WCl_6$, and 5.2 g. (0.09 mole) of ethyl acetate in a 3-neck flask was heated to 80° C. under Argon. $Me_4Sn$ (5.4 g., 0.013 mole) was added, and the reaction kept overnight at 80° C. The mixture was cooled, diluted with hexane, and extracted with conc. $NH_4OH$. After drying over $MgSO_4$, filtering, and removal of solvent, distillation gave 119 g. of recovered tridecene. Recrystallization of the residue from acetone gave 250 g. (50%) of trans-12-tetracosene, m.p. 38° C. G.c. analysis showed a purity of 99.5%.

To a solution of 452 g. (1.55 moles) of $Cp_2ZrCl_2$ in 800 mol. tetrahydrofuran under Argon was added 226.5 g. (0.776 mole) of $NaAlH_2(OCH_2CH_2OCH_3)_2$ in benzene via syringe. After stirring 2 hours at room temperature, 260.6 g. (0.776 mole) of the olefin, 12-tetracosene, was added and the mixture kept at 40° C. for 10 days. After cooling in an ice bath, solid iodine (393.2 g., 1.55 moles) was added. The solvent was removed in vacuum. The residue was dissolved in hexane, filtered, and percolated through 500 g. dry silica gel to remove impurities. NMR analysis of crude product (324.2 g. recovered) indicated an olefin: iodide ratio of 8:92. Recrystallization from acetone gave 268.5 g. pure iodide, free of olefin, m.p. 55°–6° C. (75% yield). G.c. showed the presence of about 10% tetracosane.

What is claimed is:

1. A process for preparing primary substituted n-alkane compounds, comprising:
   (a) contacting an α-olefin having a carbon chain length greater than about $C_{11}$ with an olefin metathesis catalyst which is a mixture comprising a tungsten hexahalide compound, a tetraalkyl tin compound, and ethyl acetate;
   (b) contacting the product of Step (a) with a biscyclopentadienyl zirconium hydrohalide generated in the reaction mixture; and
   (c) contacting the product of Step (b) with an electrophilic reagent selected from N-bromosuccinimide, bromine, iodine, and oxygen.

* * * * *

UNITED STATES PATENT AND TRADEMARK OFFICE
CERTIFICATE OF CORRECTION

PATENT NO. : 4,268,697
DATED : May 19, 1981
INVENTOR(S) : Thomas W. Gibson

It is certified that error appears in the above-identified patent and that said Letters Patent are hereby corrected as shown below:

Column 3, line 36, "33.4" should read -- 335.4 --.

Column 7, line 26, "800 mol." should read -- 800 ml. --.

Signed and Sealed this

Twenty-fifth Day of August 1981

[SEAL]

Attest:

GERALD J. MOSSINGHOFF

Attesting Officer

Commissioner of Patents and Trademarks